(12) United States Patent
Shimada

(10) Patent No.: US 7,324,200 B2
(45) Date of Patent: Jan. 29, 2008

(54) FLUORESCENCE PHOTOMETRIC APPARATUS

(75) Inventor: Yoshihiro Shimada, Sagamihara (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/644,730

(22) Filed: Dec. 22, 2006

(65) Prior Publication Data

US 2007/0097369 A1    May 3, 2007

Related U.S. Application Data

(63) Continuation of application No. PCT/JP2005/011292, filed on Jun. 20, 2005.

(30) Foreign Application Priority Data

Jun. 24, 2004    (JP) .............................. 2004-186352

(51) Int. Cl.
G01N 21/64    (2006.01)
(52) U.S. Cl. ................... 356/417; 356/318; 250/458.1; 359/389
(58) Field of Classification Search ................ 356/317, 356/318; 250/458.1–461.2; 359/368, 369, 359/389
See application file for complete search history.

(56) References Cited

U.S. PATENT DOCUMENTS 4,844,617 A * 7/1989 Kelderman et al. ......... 356/328

6,914,720 B2 * 7/2005 Tahara et al. ............ 250/458.1

FOREIGN PATENT DOCUMENTS

| JP | 10-90608 | 4/1998 |
|---|---|---|
| JP | 10-206742 | 8/1998 |
| JP | 2001-7173 | 1/2001 |
| JP | 2001-505997 | 5/2001 |
| JP | 2002-181710 | 6/2002 |
| JP | 2003-524180 | 8/2003 |
| JP | 2004-226252 | 8/2004 |
| JP | 2004-309458 | 11/2004 |

* cited by examiner

Primary Examiner—F. L. Evans
(74) Attorney, Agent, or Firm—Scully, Scott, Murphy & Presser, P.C.

(57) ABSTRACT

A fluorescence photometric apparatus which includes a light source, a light irradiating unit configured to condense light from the light source on a sample by means of an objective lens and irradiating the sample with the condensed light, and a photodetector which detects fluorescence emitted from the sample, includes an illuminating unit configured to obtaining a sample image, a position adjusting unit configured to adjusting a relative position of the sample and a position of a light spot condensed by the light irradiating unit, and an imaging unit configured to simultaneously two-dimensionally or three-dimensionally imaging both the sample image and an image of the light spot from the light irradiating unit configured to condensing the light on the sample.

15 Claims, 10 Drawing Sheets

F I G. 3
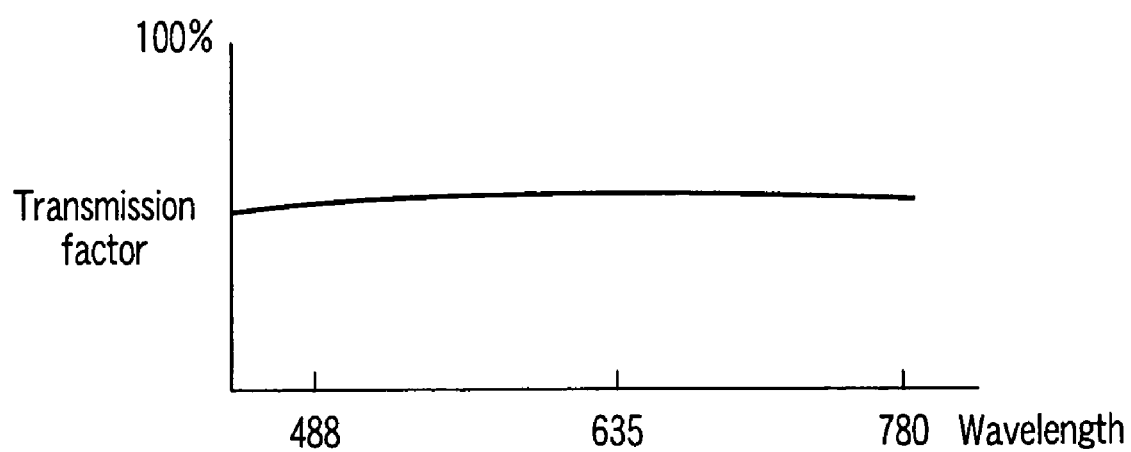
F I G. 4

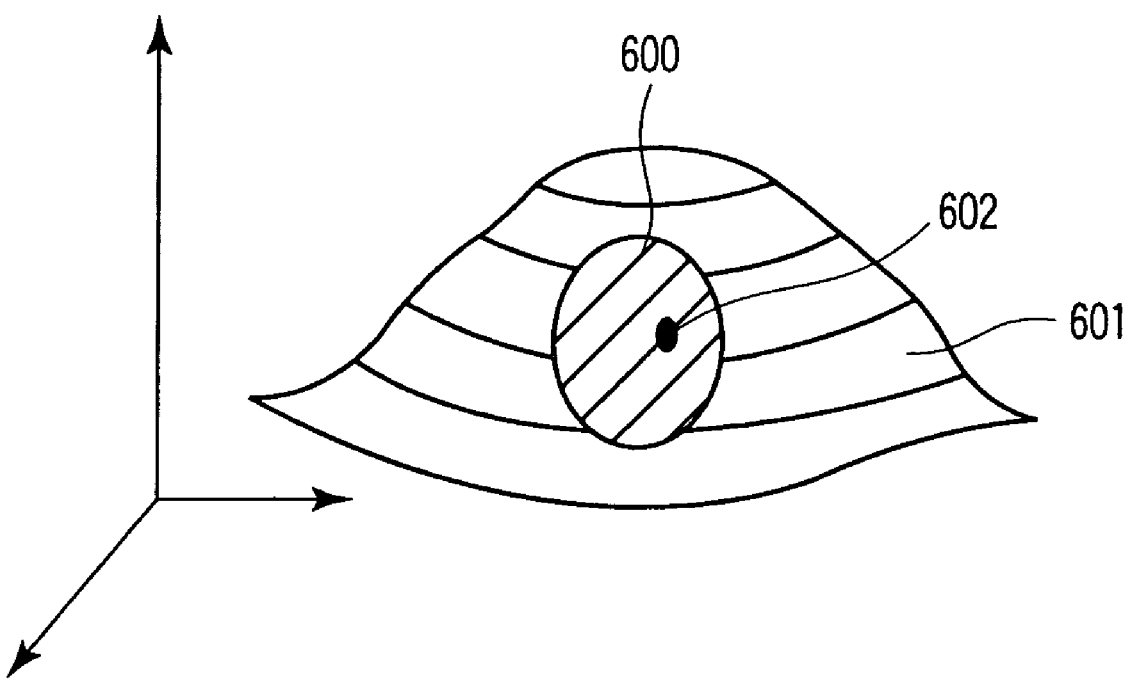
F I G. 12

FLUORESCENCE PHOTOMETRIC APPARATUS

CROSS-REFERENCE TO RELATED APPLICATIONS

This is a Continuation Application of PCT Application No. PCT/JP2005/011292, filed Jun. 20, 2005, which was published under PCT Article 21(2) in Japanese.

This application is based upon and claims the benefit of priority from prior Japanese Patent Application No. 2004-186352, filed Jun. 24, 2004, the entire contents of which are incorporated herein by reference.

BACKGROUND OF THE INVENTION

1. Field of the Invention

The present invention relates to a fluorescence photometric apparatus which optically measures fluorescence of a fluorescence-marked cell in a small region, and more particularly to a fluorescence photometric apparatus which identifies a constituent molecule of a fluorescence-marked cell.

2. Description of the Related Art

The fluorescent correlation spectroscopy is widely utilized to perform analysis such as identification of a fluorescence-marked molecule in a solution. In recent years, a target to which this analysis technology is applied is widened to a constituent molecule of a partially or entirely fluorescence-labeled cell from a fluorescent molecule in a solution. In particular, recent development of various fluorescent proteins has further accelerated a tendency of widening analysis target molecules. Furthermore, since a fluorescent protein can be developed in a specific organ in a cell by a gene manipulation, a fluorescence photometric technology including the fluorescent correlation spectroscopy is widely utilized among researchers as a strong implement for clarification of a cell function which is a source of a life phenomenon.

Moreover, when a cell or a biomedical tissue is an analysis target, an optical microscope or a laser scanning microscope is combined with a fluorescent correlation spectroscopic apparatus to be used.

PCT National Publication No. 2001-505997 discloses a fluorescent correlation spectroscopic unit which can be disposed to an optical connecting portion of a regular optical microscope. A fluorescent correlation spectroscopic module according to this technology is provided with a connecting portion and a pinhole device which allow excitation light to enter, and the connecting portion and the pinhole device are arranged on a common support. Additionally, according to this structure, coupling with an existing microscope is readily enabled, thereby obtaining a measurement result with excellent reproducibility.

PCT National Publication No. 2003-524180 discloses a photodetector which is constituted of a device constituent element for fluorescent correlation spectroscopy in at least one small amount unit and in which a measurement position for fluorescent correlation spectroscopic analysis is measured and selected in at least two-dimensional unit by utilizing an image formation type method, an image formation type microscope unit and a device constituent element are operated in a common control unit and an analysis result of at least the device constituent element is displayed as an image by means of the control unit and a computer.

According to the technology described in PCT National Publication No. 2003-524180, when a cell or the like as a measurement target is imaged by using a scanning laser microscope and a measurement target region is specified in the image, fluorescent correlation spectroscopic data in this region can be automatically obtained.

BRIEF SUMMARY OF THE INVENTION

A fluorescence photometric apparatus according to a first aspect of the present invention comprising: a light source, a light irradiating unit configured to condense light from the light source on a sample by means of an objective lens and irradiating the sample with the condensed light, and a photodetector which detects fluorescence emitted from the sample, wherein the fluorescence photometric apparatus includes an illuminating unit configured to obtaining a sample image, a position adjusting unit configured to adjusting a relative position of the sample and a position of a light spot condensed by the light irradiating unit, and an imaging unit configured to simultaneously two-dimensionally or three-dimensionally imaging both the sample image and an image of the light spot from the light irradiating unit configured to condensing the light on the sample.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a view showing spectral characteristics of a dichroic mirror;

FIG. 4 is a view showing half-transmission/half-reflection characteristics of the dichroic mirror;

FIG. 12 is a view showing a three-dimensional image.

DETAILED DESCRIPTION OF THE INVENTION

First Embodiment

Figure 1:
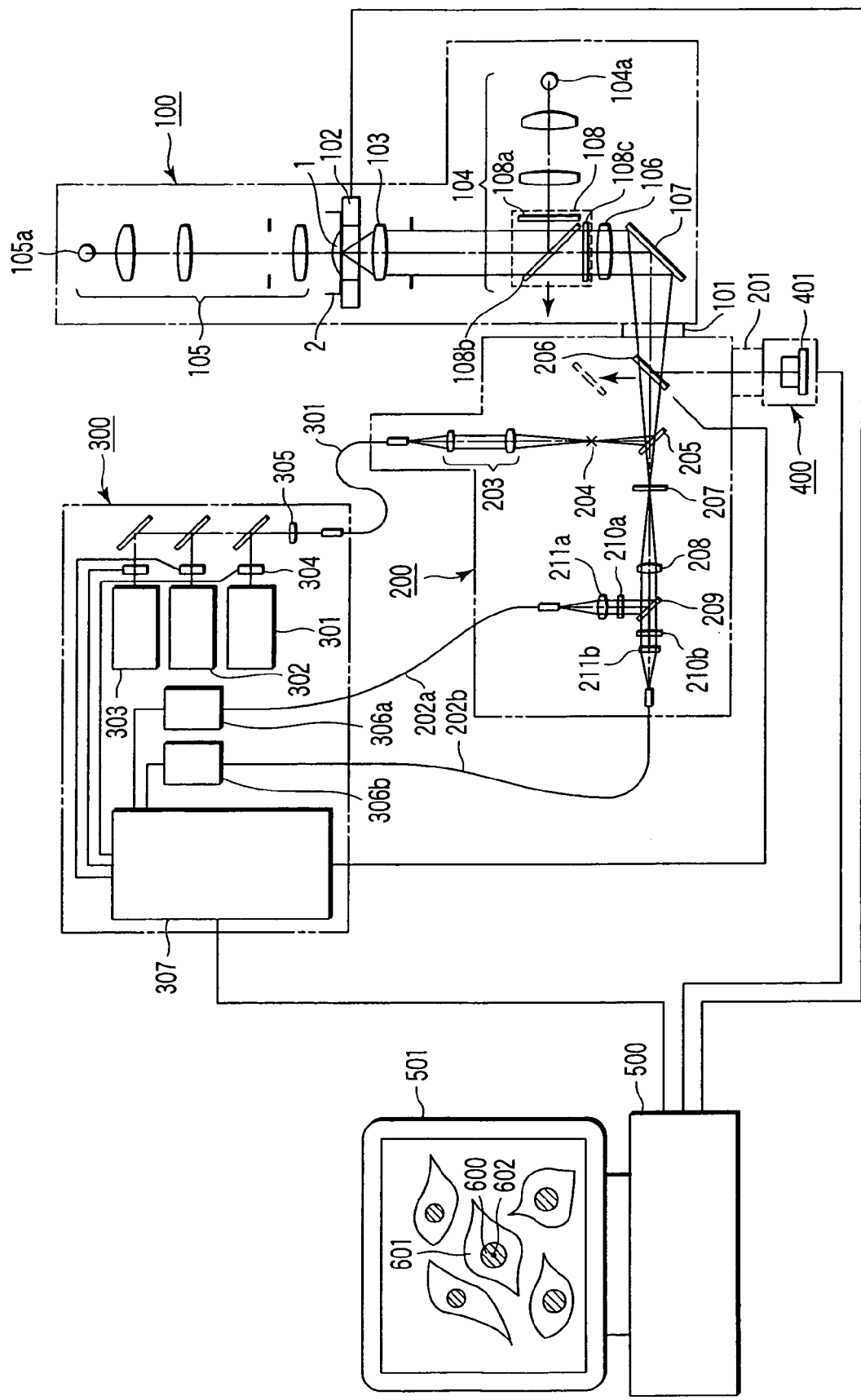
FIG. 1 is a view showing a structure of a fluorescence photometric apparatus according to a first embodiment of the present invention.

FIG. 1 is a view showing a structure of a fluorescence photometric apparatus according to a first embodiment of the present invention.

The fluorescence photometric apparatus includes an inverted microscope 100, an optical module 200, a light source/detection module 300, a CCD camera 400 and a computer 500.

An optical module 200 including a plurality of optical elements which supply excitation light to the inverted microscope 100 and optically measure fluorescence is connected with a connecting portion 101 of the inverted microscope 100. Further, the light source/detection module 300 is optically connected with this optical module 200 by means of a single-mode fiber 301. The light source/detection module 300 includes a light source of excitation light and a detector of fluorescence. Furthermore, the optical module 200 has a connecting portion 201, and the CCD camera 400 which captures an observation image of, e.g., a cell of the inverted microscope 100 is connected with this connecting portion. An electric signal from the CCD camera 400 is supplied to the computer 500 having a non-illustrated built-in processing board, and a processed image or the like is displayed on a monitor 501.

A structure of the inverted microscope 100 will now be described.

A sample 1 is a cultured cell, and a nucleus and a microtubule thereof are fluorescent-marked with DRAQ5 and GFP, respectively. Here, DRAQ5 emits fluorescence having a peak at 670 nm when excited in the vicinity of 635 nm. Moreover, GFP emits fluorescence having a peak at 520 nm when excited in the vicinity of 488 nm.

The sample 1 is cultured in a petridish 2, and mounted on an electric XY stage 102. The electric XY stage 102 is connected to the computer 500 by means of a non-illustrated controller, and driven and controlled based on an instruction from the computer 500. An objective lens 103 can be manually or electrically driven in a direction of an optical axis by a non-illustrated guide mechanism, and can perform focus adjustment.

A reflecting fluorescence illumination optical system 104 including a xenon lamp 104a and a transmitting illumination optical system 105 including a halogen lamp 105a are provided to obtain an image of the sample 1. An analyzer can use the reflecting fluorescence illumination optical system 104 or the transmitting illumination optical system 105 as required.

Figure 2A:
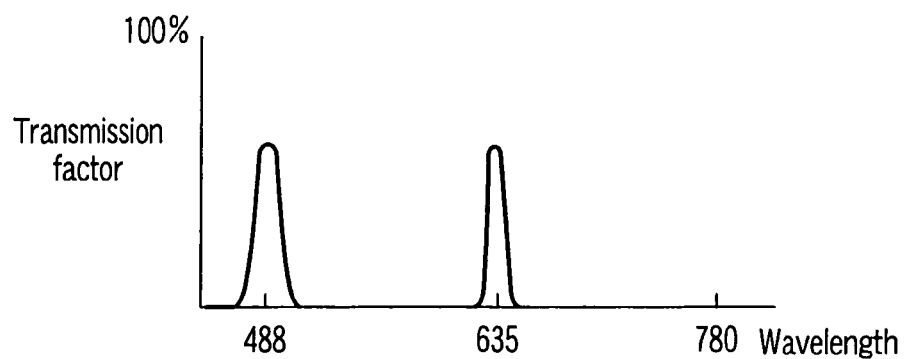
FIG. 2A is a view showing spectral characteristics of each optical element constituting a fluorescence observation cube.
Figure 2B:
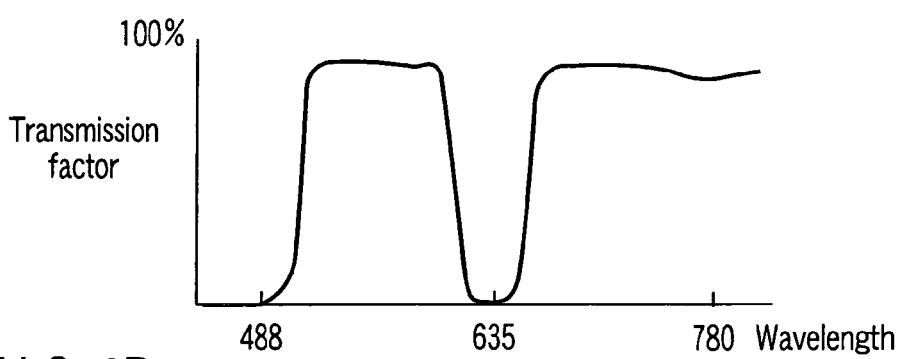
FIG. 2B is a view showing spectral characteristics of each optical element constituting the fluorescence observation cube.
Figure 2C:
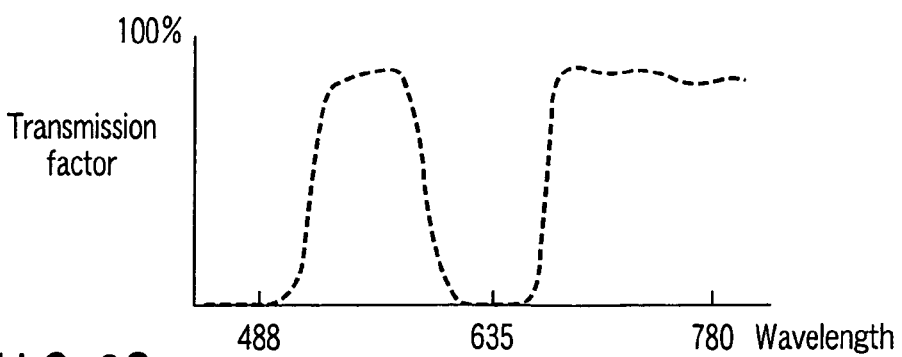
FIG. 2C is a view showing spectral characteristics of each optical element constituting the fluorescence observation cube.

The reflecting fluorescence illumination optical system 104 includes a fluorescence observation cube 108 formed of an excitation filter 108a, a dichroic mirror 108b and a barrier filter 108c, and the fluorescence observation cube 108 is arranged on a switching device (not shown) so that it can be inserted into/removed from an optical path. FIGS. 2A, 2B and 2C are views showing spectral characteristics of each optical element constituting the fluorescence observation cube 108. FIG. 2A shows spectral characteristics of the excitation filter 108a, FIG. 2B shows spectral characteristics of the dichroic mirror 108b and FIG. 2C shows spectral characteristics of the barrier filter 108c. As a result, transmission/reflection of light from the illumination optical system and a laser beam (which will be described later) can be controlled to simultaneously illuminate and observe the cultured cell fluorescent-marked with GFP and DRAQ5.

Upon being illuminated by the illumination system, an image of the sample 1 creates a magnified image on an image forming surface of an image forming lens 106 by means of the objective lens 103, the dichroic mirror 108b, the barrier filter 108c, the image forming lens 106 and a mirror 107.

An operation of the fluorescence photometric apparatus will now be described.

In the light source/detection module 300 are arranged a solid laser 301 which oscillates a laser beam having a wavelength of 488 nm, a semiconductor laser 302 which oscillates a laser beam having a wavelength of 635 nm and a semiconductor laser 303 which oscillates a laser beam having a wavelength of 780 nm together with shutters 304 corresponding to the respective lasers. Laser beams exiting from the respective lasers are combined by means of an appropriate dichroic mirror or mirror, and led to the optical module 200 via a condenser lens 305 and the single-mode fiber 301.

The laser beam exiting from the single-mode fiber 301 is condensed on a condensing position 204 by means of the lens 203. It is to be noted that the condensing position 204 is set to an image forming position of the image forming lens 106. Further, an NA of emission of the lens 203 is set in such a manner that a diameter of an incident beam to the objective lens substantially satisfies a pupil of the objective lens.

The laser beam is reflected by a dichroic mirror 205 having such spectral characteristics as shown in FIG. 3, and transmitted through a beam splitter 206 having such half-transmission/half-reflection characteristics as shown in FIG. 4. Furthermore, it enters the objective lens 103 by means of the mirror 107 and the image forming lens 106 to be condensed on the sample 1, thereby forming a light spot.

Light (e.g., reflected/scattered/fluorescent) from the sample 1 irradiated with the laser beam travels along an optical path in an opposite direction, and the beam splitter 206 is irradiated with this light together with light (e.g., transmitted/reflected/scattered/fluorescent) from the sample illuminated by the reflecting fluorescence illumination optical system 104 or the transmitting illumination optical system 105. In the beam splitter 206, an approximately half of a light quantity of applied light is reflected by the characteristics shown in FIG. 4 and enters a CCD imaging element 401 in the CCD camera 400. Since this CCD imaging element 401 is arranged at the image forming position of the image forming lens 106, an observation image of the sample and a light spot image of the laser beam can be obtained. The captured images are supplied to the computer 500 and displayed on the monitor 501.

It is to be noted that the beam splitter 206 is configured to be inserted into/removed from an optical path by non-illustrated switching means, and it deviates from the optical path when effecting fluorescence photometry from the sample without carrying out observation of the sample. It is to be noted that this operation may be performed in cooperation with selection of a laser beam as will be described later.

Figure 5A:
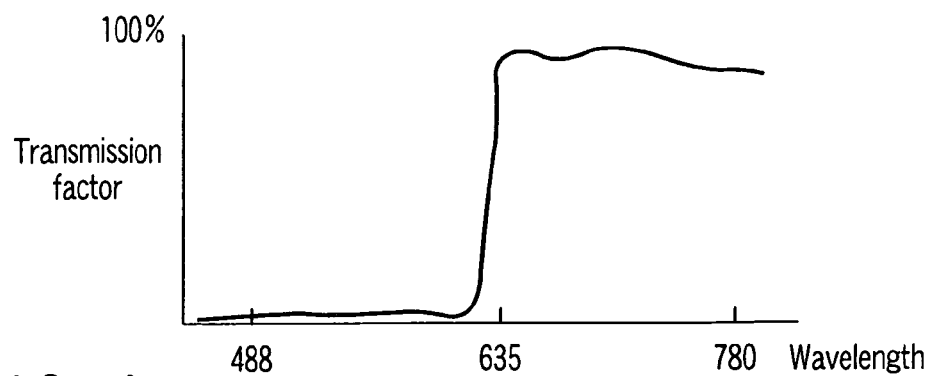
FIG. 5A is a view showing spectral characteristics of the dichroic mirror and a barrier filter.
Figure 5B:
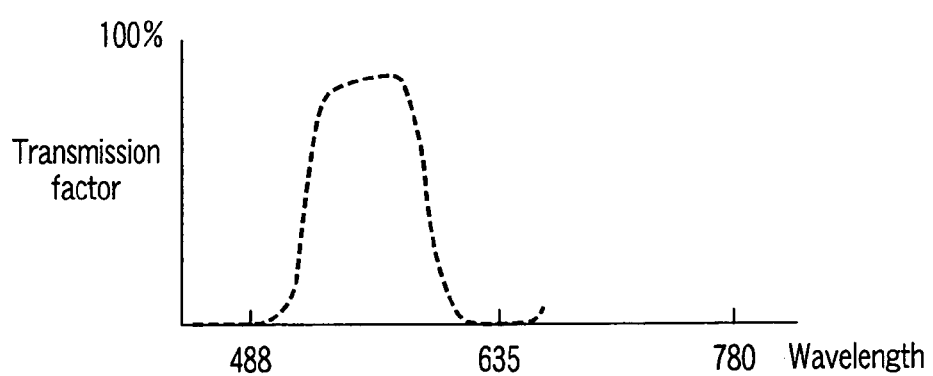
FIG. 5B is a view showing spectral characteristics of the dichroic mirror and the barrier filter.
Figure 5C:
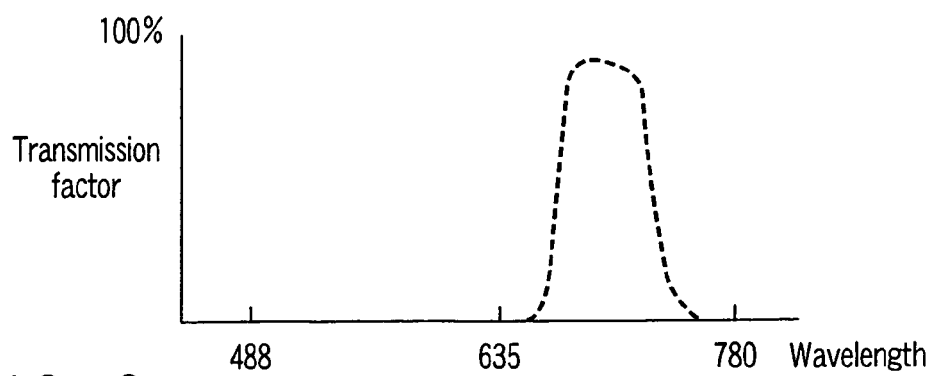
FIG. 5C is a view showing spectral characteristics of the dichroic mirror and the barrier filter.

A pin hole 207 is arranged at a focusing position of the image forming lens 106, thereby constituting a confocal optical system. Moreover, light from the sample 1 transmitted through the pin hole 207 is converted into parallel light by a collimator lens 208, and enters a dichroic mirror 209 having spectral characteristics shown in FIG. 5A. Based on such spectral characteristics, fluorescence from the nucleus of the sample marked with DRAQ5 is transmitted through the dichroic mirror 209, and fluorescence from the microtubule (GFP) is reflected by the dichroic mirror 209. Barrier filters 210a and 210b having spectral characteristics shown in FIGS. 5B and 5C are arranged in the respective optical paths so that fluorescence from the sample 1 alone can be transmitted through these filters, and each fluorescence is led to the light source/detection module 300 by means of condenser lenses 211a and 211b and multi-mode fibers 202a and 202b.

Avalanche photodiodes 306a and 306b capable of effecting high-speed photon counting are connected with the multi-mode fibers 202a and 202b along which light from the optical module 200 is transmitted, and their measurement outputs are supplied to a communication/control board 307. Additionally, the communication/control board 307 transmits its measurement output to the computer 500, and the computer 500 executes fluorescent correlation analysis based on its measurement value. It is to be noted that the communication/control board 307 is configured to control opening/closing the shutters 304 corresponding to the respective lasers and control oscillation outputs from the respective lasers in response to a command from the computer 500.

A measurement procedure using the fluorescence photometric apparatus according to this embodiment will now be described in detail.

A sample image is displayed in a step 1.

The sample is illuminated by the reflecting fluorescence illumination optical system 104, a focal point is adjusted with respect to the nucleus which is a target sample region, and an image 600 of the nucleus of the sample marked with DRAQ5 and an image 601 of the microtubule marked with GFP are displayed on the monitor 501 by the CCD camera 400. It is to be noted that display may be continuously carried out at an appropriate shutter speed of the CCD.

The shutters are controlled to select a light source in a step 2.

The shutter 304 set in the optical path of the semiconductor laser 303 which oscillates a laser beam having a wavelength of 780 nm is opened in response to a command from the computer 500, and the sample 1 is irradiated with the laser beam. It is to be noted that the shutters 304 corresponding to the other lasers are closed.

Sighting of the sample is carried out in a step 3.

Since a laser spot 602 from the semiconductor laser 303 which oscillates a laser beam having a wavelength of 780 nm is displayed on the monitor 501, the electric stage 102 is drive to move the cell so that a desired position of the cell is irradiated with the laser spot 602. In this embodiment, the nucleus of the cell is sighted. It is to be noted that the nucleus is marked with DRAQ5 and hence it is not excited by the semiconductor laser 303 which oscillates a laser beam having a wavelength of 780 nm. Therefore, a color of the sample 1 is not degraded at all while a target position is sighted.

Optical elements which are not required for fluorescence photometry are moved away in a step 4.

The fluorescence observation cube 108 and the beam splitter 206 are moved away from the optical path.

In a step 5, the shutters are controlled to select a light source.

The shutter 304 which is set in the optical path of the semiconductor laser 303 which oscillates a laser beam having a wavelength of 780 nm is closed, and the shutter 304 which is set in the optical path of the semiconductor laser 302 which oscillates a laser beam having a wavelength of 635 nm is opened.

In a step 6, fluorescence photometry is carried out.

Fluorescence photometry of the nucleus marked with DRAQ5 is started, and photometric data is transferred to the computer 500.

In a step 7, the shutters are controlled.

Upon completion of photometry, the shutter 304 set in the optical path of the semiconductor laser 303 which oscillates a laser beam having a wavelength of 635 nm is closed.

It is to be noted that controlling means by which the beam splitter 206 is inserted/removed in accordance with selection of the laser beam source may be provided in the above-described procedure.

Although the above has described the procedure of performing fluorescence photometry of the nucleus marked with DRAQ5, but the semiconductor laser 301 which oscillates a laser beam having a wavelength of 488 nm may emit the laser beam to effect photometry of the microtubule marked with GFP or carry out photometry while switching both the objects. Further, in order to obtain a sample image, an image illuminated by the transmitting illumination optical system 105 may be displayed, or the sample image obtained from illumination by both the transmitting illumination optical system 105 and the reflecting fluorescence illumination optical system 104 may be displayed.

Furthermore, an LED may be used in place of each laser. Since an LED having substantially the same wavelength as that of the laser exists, using the LED can inexpensively constitute a small fluorescence photometric apparatus.

Incidentally, it is desirable for a wavelength of the sighting laser 301 to be longer that those of the measurement lasers 302 and 303. That is because light having a long wavelength has a lower energy than that of light having a short wavelength, and hence it does not adversely affect to disturb measurement of the sample. Moreover, a step of effecting fluorescence photometry while automatically finely adjusting a focal point may be added to the above-described steps. As a result, fluorescent correlation data in a depth direction of the cell can be obtained.

[Effects of First Embodiment]

In the first embodiment, the semiconductor laser 303 is provided as a laser which sights the sample besides the lasers which excite the sample. Additionally, their laser beams are combined and led to the irradiation optical system by using one single-mode fiber. Therefore, a sighting position can be matched with a measurement position, thus improving reliability of data.

Additionally, observation of the sighting position and fluorescence measurement can be readily switched and confirmed by inserting/removing the beam splitter 206 into/from the optical path.

Further, since the optical module 200 includes the connecting portion 201 with respect to the CCD camera and the lens 203 which leads light from the light source/detection module 300, the CCD camera or a picture shooting device can be used by just disposing such a device to the connecting portion of the microscope. Of course, the optical module 200 may be integrally configured with the CCD camera.

In this embodiment, although the optical module 200 is connected with the inverted microscope, it can be attached to a connecting portion of an erected microscope, thereby providing the fluorescence photometric apparatus superior in system properties. Furthermore, since the avalanche photodiodes are built in the light source/detection module 300, there is an advantage that the optical module 200 can be reduced in size.

Second Embodiment

In a second embodiment, structures of an inverted microscope 100 and an optical module 200 are different from those in the first embodiment. Therefore, like reference numerals denote parts equal to those in the first embodiment, thereby omitting a detailed explanation thereof.

Figure 6:
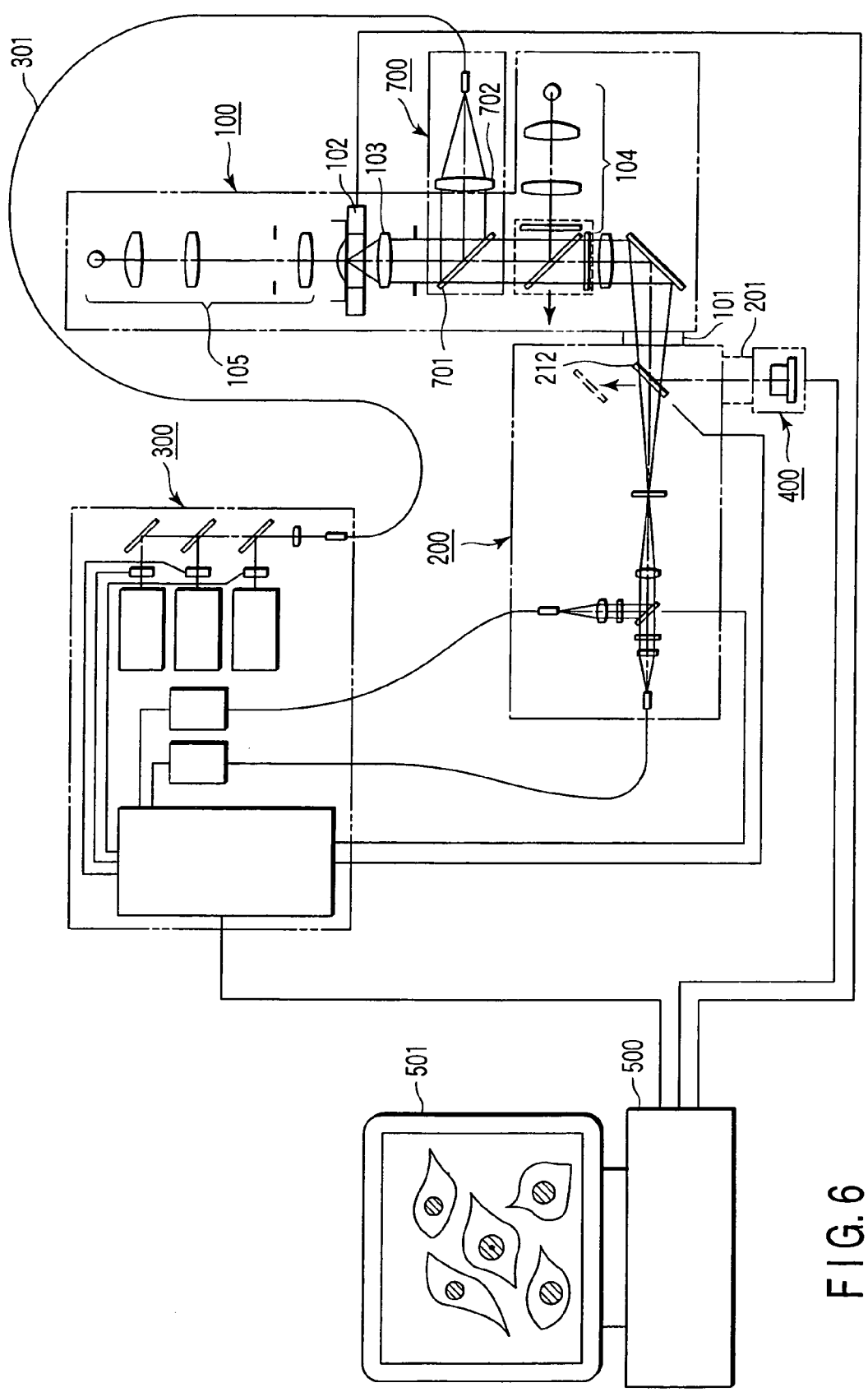
FIG. 6 is a view showing a structure of a fluorescence photometric apparatus according to a second embodiment of the present invention.

FIG. 6 is a view showing a structure of a fluorescence photometric apparatus according to the second embodiment of the present invention.

The inverted microscope 100 is different from that of the first embodiment in that this microscope includes a collimator lens unit 700 which leads a laser beam from a light source/detection module 300, and other structures are the same as those in the first embodiment.

Figure 7:
FIG. 7 is a view showing spectral characteristics of a dichroic mirror.

An optical module 200 for fluorescence photometry is connected with the inverted microscope 100 by means of a connecting portion 101, and the light source/detection module 300 is connected with the inverted microscope 100 by means of a single-mode fiber 301 and the collimator lens unit 700. Moreover, a dichroic mirror 701 and a collimator lens 702 having spectral characteristics shown in FIG. 7 are provided in the collimator lens unit 700.

The optical module 200 is different from that of the first embodiment in that a mechanism which leads a laser beam from the light source/detection module 300 is not provided and that a total-reflection mirror 212 is provided in place of the beam splitter 206, and other structures are the same as those in the first embodiment.

The optical module 200 has a connecting portion 201, and a CCD camera 400 is connected with this portion. An electric signal from the CCD camera 400 is supplied to a computer 500 having a non-illustrated built-in processing board, and an obtained image is displayed on a monitor 501. Of course, the optical module 200 may be integrally configured with the CCD camera.

It is to be noted that the configuration of the light source/detection module 300 is the same as that in the first embodiment.

An operation of the fluorescence photometric apparatus will now be described.

A laser beam from the light source/detection module 300 is applied to a sample 1 via the collimator lens unit 700 and an objective lens 103, thereby generating a light spot. Both light (e.g., reflected/scattered/fluorescent) from the sample 1 and light from the sample (e.g., transmitted/reflected/scattered/fluorescent) illuminated by a reflecting fluorescence illumination optical system 104 or a transmitting illumination optical system 105 are led to the optical module 200, reflected by the total-reflection mirror 212, and applied to the CCD camera 400. This CCD imaging element 401 is arranged at an image forming position of an image forming lens 106, and hence an observation image of the sample and an image of the light spot can be obtained. The captured images are transmitted to the computer 500 and displayed on the monitor 501.

It is to be noted that the total-reflection mirror 212 is configured to be inserted into/removed from optical path by non-illustrated switching means so that it deviates from an the optical path when a laser beam from the optical module 300 is applied to perform fluorescence photometry from the sample 1. This inserting/removing operation may be effected in cooperation with selection of a laser beam. Other structures are the same as those in Embodiment 1.

Additionally, the measurement procedure using the fluorescence photometric apparatus according to the second embodiment is also the same as that in the first embodiment, thereby omitting a detailed explanation thereof.

[Effects of Second Embodiment]

In the second embodiment, a light leading portion which leads light from the light source/detection module 300 is not mounted in the optical module 200, and hence this optical module can be configured to be smaller than the structure in the first embodiment.

Further, since the total-reflection mirror 212 is used in place of the dichroic mirror, light from the sample 1 can be supplied to the CCD camera 400 while suppressing a light loss.

Third Embodiment

A third embodiment is different from the first embodiment in that one laser uses both a sighting function and a measurement function to provide the minimum module structure. Therefore, like reference numerals denote parts equal to those in the first embodiment, thereby omitting a detailed explanation thereof.

Figure 8:
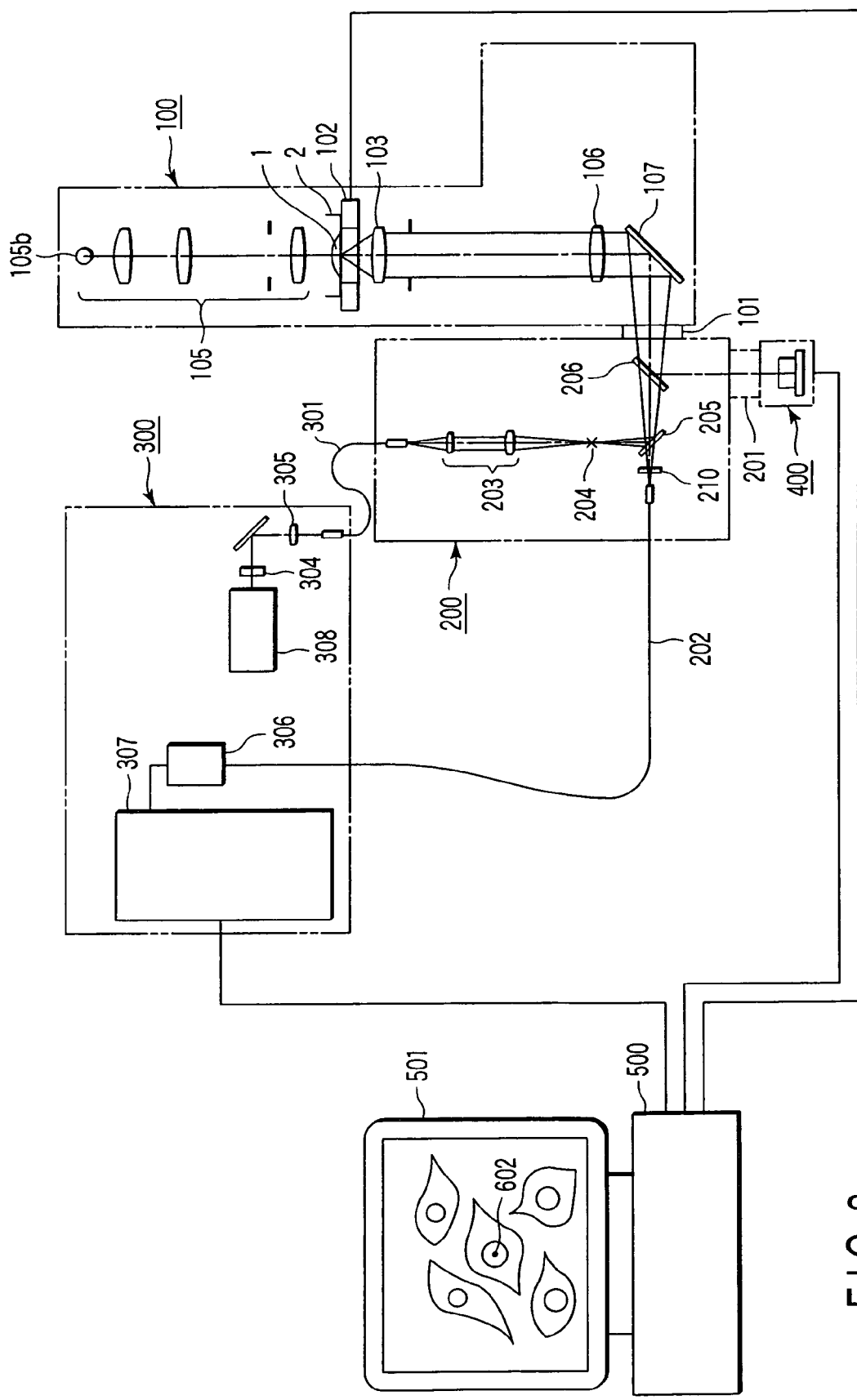
FIG. 8 is a view showing a structure of a fluorescence photometric apparatus according to a third embodiment of the present invention.

FIG. 8 is a view showing a structure of a fluorescence photometric apparatus according to the third embodiment of the present invention.

An optical module 200 including a plurality of optical elements which supply excitation light to an inverted microscope 100 and perform photometry of fluorescence is connected with a connecting portion 101 of the inverted microscope 100. Further, a light source/detection module 300 is optically connected with this optical module 200 by means of a single-mode fiber 301. The light source/detection module 300 includes a light source for excitation light and a fluorescence detector.

Furthermore, the optical module 200 has a connecting portion 201, and a CCD camera 400 which captures an observation image of a cell or the like in the inverted microscope 100 is connected with this portion. An electric signal of the CCD camera 400 is supplied to a computer 500 having a non-illustrated built-in processing board, and a processed image or the like is displayed on the monitor 501. Of course, the optical module 200 may be integrally configured with the CCD camera 400.

A sample 1 is a cultured cell, and its nucleus is fluorescent-marked with DAPI. The sample 1 is cultured in a petridish 2 and mounted on an electric XY stage 102 of the microscope. The electric XY stage 102 is connected with the computer 500 via a non-illustrated controller, and driven and controlled based on an instruction from the computer 500. An objective lens 103 can be manually or electrically driven in a direction of an optical axis by a non-illustrated guide mechanism, and can perform focus adjustment.

Moreover, a transmitting illumination optical system 105 including an LED 105b which emits light of 680 nm is provided in the inverted microscope 100 in order to obtain an image of the sample 1.

An operation of the fluorescence photometric apparatus will now be described.

A semiconductor laser 308 which oscillates a laser beam having a wavelength of 405 nm is arranged together with a shutter 304 in the light source/detection module 300. The laser beam is led to the optical module 200 by means of a condenser lens 305 and a single-mode fiber 301.

The laser beam exiting from the single-mode fiber 301 is condensed on a condensing position via a lens system 203. It is to be noted that the condensing position 204 is set to an image forming position of an image forming lens 106. Additionally, an NA of emission of the lens 203 is set in such a manner that a diameter of a beam entering the objective lens substantially satisfies a pupil of the objective lens.

Figure 9A:
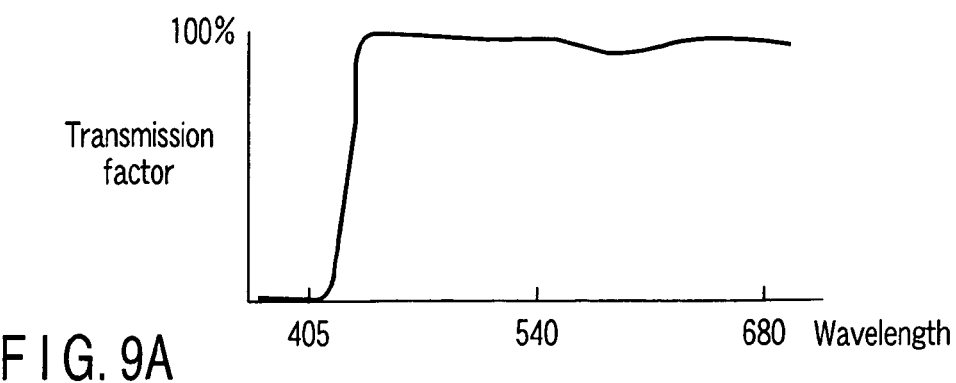
FIG. 9A is a view showing spectral characteristics of a dichroic mirror and a barrier filter.
Figure 10:
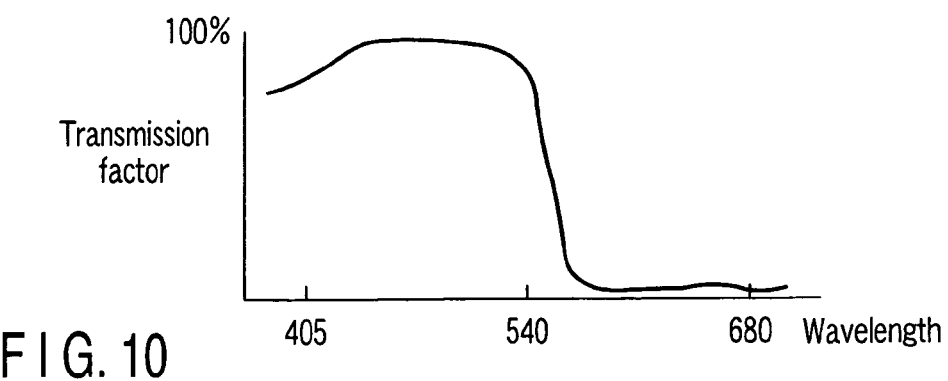
FIG. 10 is a view showing spectral characteristics of the dichroic mirror.

The laser beam is reflected by a dichroic mirror 205 having such spectral characteristics as shown in FIG. 9A, and transmitted through a fixedly arranged beam splitter 206 having such spectral characteristics as shown in FIG. 10. Based on such spectral characteristics, approximately 80% of light having a wavelength of 405 nm is transmitted. Further, this light enters the objective lens 103 via a mirror 107 and the image forming lens 106 and is condensed on the sample 1, thereby forming a light spot.

Light (e.g., reflected/scattered/fluorescent) from the sample 1 irradiated with the laser beam travels along an optical path in an opposite direction, and the beam splitter 206 is irradiated with this light and light (e.g., transmitted/reflected/scattered/fluorescent) from the sample illuminated by the transmitting illumination optical system 105. In the beam splitter 206, light reflected in accordance with the spectral characteristics shown in FIG. 10 enters a CCD imaging element 401 in the CCD camera 400. Since this CCD imaging element 401 is arranged at the image forming position of the image forming lens 106, thus obtaining an observation image of the sample and an image of the light spot. The captured images are supplied to the computer 500 and displayed on the monitor 501. That is, a transmitted image and an image of a laser spot having a wavelength of 405 nm are displayed on the monitor 501.

Figure 9B:
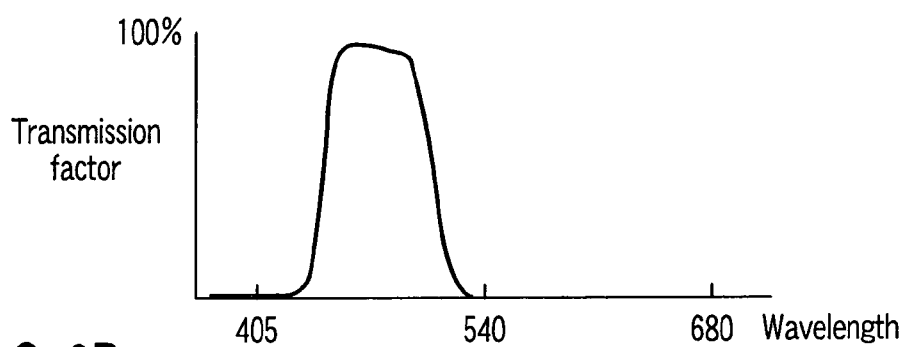
FIG. 9B is a view showing spectral characteristics of the dichroic mirror and the barrier filter.

On the other hand, in regard to light including fluorescence based on DAPI from the sample 1, the fluorescence based on DAPI alone is transmitted through a barrier filter 210 having such spectral characteristics as shown in FIG. 9B and enters a multi-mode fiber 202. It is to be noted that an end surface of the multi-mode fiber 202 having an appropriate core diameter is arranged at the image forming position of the image forming lens 106 to function as a confocal optical system. Furthermore, the fluorescence based on DAPI is led to the light source/detection module 300 via the multi-mode fiber 202.

An avalanche photodiode 306 capable of performing high-speed photon counting is connected with the multi-mode fiber 202 along which light from the optical module 200 is transmitted, and its measurement output is supplied to a communication/control board 307. Furthermore, the communication/control board 307 supplies its measurement output to the computer 500, and the computer 500 executes fluorescent correlation analysis based on its measurement value. It is to be noted that the communication/control board 307 is configured to control opening/closing of the shutter corresponding to each laser and control an oscillation output from each laser in response to an instruction from the computer 500.

A measurement procedure using the fluorescence photometric apparatus according to this embodiment will now be described in detail.

A sample image is displayed in a step 1.

The transmitting illumination optical system 105 illuminates the sample, and a transmission image of the sample 1 is displayed on the monitor 501 by the CCD camera 400. Incidentally, it is good enough to continuously perform display at an appropriate shutter speed of the CCD.

In a step 2, the shutters are controlled to select a light source.

The shutter 304 set in an optical path of the semiconductor laser 308 is opened to irradiate the sample 1 with a laser beam in response to a command from the computer 500.

In a step 3, the sample is sighted.

Since a laser spot 602 is displayed on the monitor 501, the electric stage 102 is driven to be moved to a target position on a cell in such a manner that a desired position on the cell is irradiated with the laser spot 602. In this embodiment, a nucleus of the cell is sighted. It is to be noted that since the nucleus is marked with DAPI, no excitation occurs with the LED 105b which emits light having a wavelength of 680 nm, and hence a color of the sample 1 is not degraded while sighting the target position.

In a step 4, fluorescence photometry is carried out.

Fluorescence photometry is started, and photometric data is transferred to the computer 500.

In a step 5, the shutters are controlled.

Upon completion of photometry, the shutter 304 is closed.

[Effects of Third Embodiment]

In the third embodiment, the beam splitter 206 is fixedly arranged, and hence no driving portion is provided. Therefore, the reliable and inexpensive fluorescence photometric apparatus can be provided.

Further, the semiconductor laser 308 which oscillates a laser beam having a wavelength of 405 nm is used as a laser, and the single laser is configured to perform both sighting and measurement. Accordingly, the minimum structure of the apparatus can be provided.

Fourth Embodiment

A fourth embodiment is different from the first embodiment in that a confocal laser scanning microscope is used to constitute an apparatus. Therefore, like reference numerals denote parts equal to those in the first embodiment, thereby omitting a description thereof.

Figure 11:
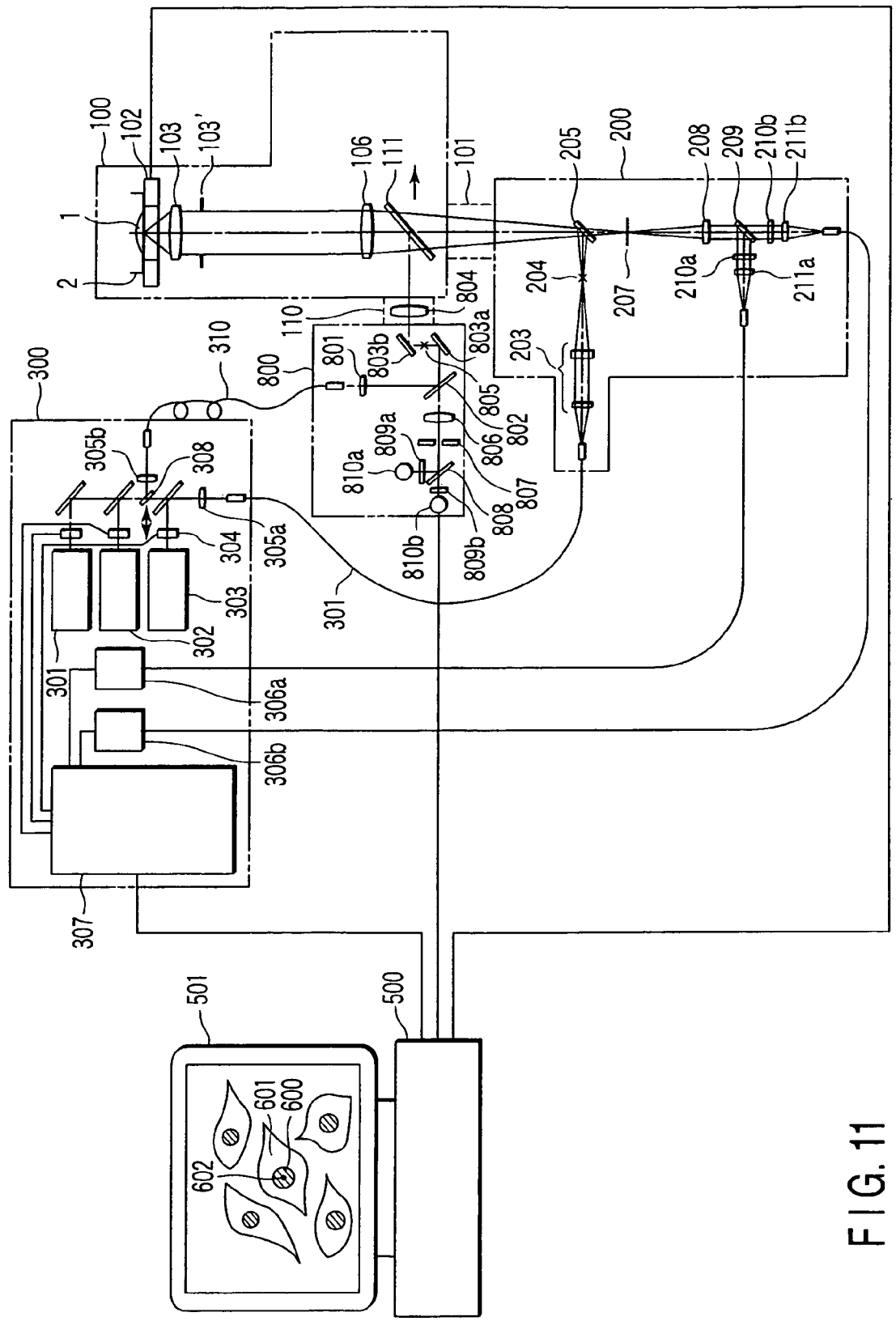
FIG. 11 is a view showing a structure of a fluorescence photometric apparatus according to a fourth embodiment of the present invention.

FIG. 11 is a view showing a structure of a fluorescence photometric apparatus according to the fourth embodiment of the present invention.

An optical module 200 including a plurality of optical elements which supply excitation light to an inverted microscope 100 and perform photometry of fluorescence is connected with a connecting portion 101 provided on a bottom surface portion of the inverted microscope 100. Furthermore, a light source/detection module 300 is optically connected with this optical module 200 via a single-mode fiber 301. The light source/detection module 300 includes a light source for excitation light and a fluorescence detector. Moreover, a confocal laser scanning microscope module 800 is connected with a connecting portion 110 provided on a side surface portion of the inverted microscope 100. An output signal from the confocal laser scanning microscope module 800 is supplied to a computer 500 having a non-illustrated built-in processing board, and a processed image or the like is displayed on a monitor 501.

The inverted microscope 101 will now be described.

A sample 1 is a cultured cell, and a nucleus and a microtubule thereof are fluorescence-marked with DRAQ5 and GFP, respectively. The sample 1 is cultured in a petridish 2 and mounted on an electric XY stage 102 of the microscope. The electric XY stage 102 is connected with the computer 500 via a non-illustrated controller, and driven and controlled based on an instruction from the computer 500. An objective lens 103 can be manually or electrically driven in a direction of an optical axis by a non-illustrated guide mechanism, and can perform focus adjustment. Moreover, a beam splitter 111 having half-transmission/half-reflection characteristics shown in FIG. 4 is arranged on a switching device (not shown) so that in can be inserted into/removed from an optical axis. It is to be noted that a transmitting illumination optical system or a reflecting fluorescence illumination optical system is not shown in order to avoid complexity, but these systems may be provided like the first embodiment.

An operation of the fluorescence photometric apparatus will now be described.

In the light source/detection module 300, a solid laser 301 which oscillates a laser beam having a wavelength of 488 nm, a semiconductor laser 302 which oscillates a laser beam having a wavelength of 635 nm and a semiconductor laser 303 which oscillates a laser beam having a wavelength of 780 nm are arranged together with shutters corresponding to the respective lasers. Laser beams emitted from the respective lasers 301 and 302 are combined by means of an appropriate dichroic mirror.

When a mirror 308 which is arranged to allow insertion/removal thereof is inserted in an optical path, the combined laser beam is reflected and led to the confocal laser scanning microscope module 800 via a condenser lens 305b and a single-mode fiber 310. On the other hand, when the mirror 308 which is arranged to allow insertion/removal thereof is out of the optical path, the combined laser beam travels straight ahead and is further combined with the semiconductor laser 303 which oscillates a laser beam having a wavelength of 780 nm. Additionally, the laser beam is led to the optical module 200 by means of the condenser lens 305a and the single-mode fiber 301.

The laser beam led to the confocal laser scanning microscope module 800 along the single-mode fiber 310 is converted into parallel light by a collimator lens 801 and reflected by a dichroic mirror 802 having spectral characteristics shown in FIG. 4. The reflected laser beam is two-dimensionally optically scanned by galvanometer mirrors 803a and 803b and enters the inverted microscope 100 via a pupil projection lens 804. It is to be noted that an intermediate position 805 between the galvanometer mirrors 803a and 803b is substantially projected onto a pupil position of the objective lens 103, i.e., a rear focal position 103' via the pupil projection lens 804, the beam splitter 111 and an image forming lens 106.

As a result, the laser beam exiting from the objective lens 103 is condensed on the sample 1 and two-dimensionally scans the sample 1. Fluorescence (the nucleus: DRAQ, the microtubule: GFP) produced by the sample 1 returns along the optical path in an opposite direction, is transmitted through the dichroic mirror 802, further transmitted through a confocal lens 806 and a pin hole 807 and enters a dichroic mirror 808 having spectral characteristics shown in FIG. 5A.

The fluorescence from the sample 1 diverges in accordance with the spectral characteristics of the dichroic mirror 808. That is, DRAQ of the nucleus is transmitted and GFP of the microtubule is reflected. Fluorescence alone is taken out from these lights by barrier filters 809a and 809b having spectral characteristics shown in FIGS. 5B and 5C, and detected by photo-multipliers 810a and 810b. Detection signals from these members are input to the computer 500 where these signals are processed, and respective images of the nucleus: DRAQ and the microtubule: GFP are displayed on the monitor 501.

The laser beam led to the optical module 200 along the single-mode fiber 301 is condensed on a condensing position 204 via the lens 203. It is to be noted that the condensing position 204 is set at an image forming position of the image forming lens 106. Additionally, an NA of emission of the lens 203 is set in such a manner that a diameter of a beam entering the objective lens substantially satisfies a pupil of the objective lens. The laser beam is reflected by a dichroic mirror 205 having spectral characteristics shown in FIG. 3, enters the inverted microscope 100, further enters the objective lens 103 via the beam splitter 111 and the image forming lens 106, and is condensed on the sample 1, thereby forming a light spot.

Light (e.g., reflected/scattered/fluorescent) from the sample 1 irradiated with the laser beam travels along an optical path in an opposite direction, an approximately half of its light quantity is reflected together with light (e.g., transmitted/reflected/scattered/fluorescent) from the sample optically scanned by the confocal laser scanning microscope module 800 by the beam splitter 111, then this light returns to the confocal laser scanning microscope module 800, and is displayed on the monitor 501 as described above.

On the other hand, when performing fluorescence photometry, since the beam splitter 111 is deviated from the optical path by switching means (not shown), light from the sample enters the optical module 200. A pin hole 207 provided in the optical module 200 is arranged at a focal position of the image forming lens 106, thus constituting a confocal optical system. Light from the sample 1 which has been transmitted through the pin hole 207 is converted into parallel light by the collimator lens 208, and enters a dichroic mirror 209 having spectral characteristics shown in FIG. 5A.

Based on such spectral characteristics, fluorescence from the nucleus (DRAQ5) of the sample is transmitted, and fluorescence from the microtubule (GFP) is reflected. Barrier filters 210a and 210b are arranged in respective optical paths to transmit fluorescence alone from the sample 1 therethrough, and each fluorescence is led to multi-mode fibers 202a and 202b via condenser lenses 211a and 211b and supplied to the light source/detection module 300.

Avalanche photodiodes 306a and 306b capable of performing high-speed photon counting are connected with the multi-mode fibers 202a and 202b along which light from the optical module 200 is transmitted, and their measurement outputs are supplied to a communication/control board 307. Further, the communication/control board 307 transmits its measurement output to the computer 500, and the computer 500 executes fluorescent correlation analysis based on its measurement value. It is to be noted that the communication/control board 307 is configured to control opening/closing of the shutters 304 corresponding to the respective lasers and control oscillation outputs from the respective lasers in response to a command from the computer 500.

A measurement procedure using the fluorescence photometric apparatus according to this embodiment will now be described in detail.

In a step 1, a sample image is displayed.

The shutters 304 corresponding to the solid laser 301 which oscillates a laser beam having a wavelength of 488 nm and the semiconductor laser 302 which oscillates a laser beam having a wavelength of 635 nm are opened, the mirror 308 is inserted into an optical path, and laser beams are transmitted to the confocal laser scanning microscope module 800.

The sample 1 is irradiated by using the confocal laser scanning microscope module 800, a focal point is adjusted with respect to a target sample region (a nucleus in this example), and output signals from the photo-multipliers 810a and 810b are output to the computer 500. The computer 500 displays an image 600 of the nucleus of the sample marked with DRAQ5 and an image 601 of the microtubule marked with GFP on the monitor 501. Incidentally, it is good enough to continuously perform display at a speed corresponding to a scanning speed of the confocal laser scanning microscope module 800.

In a step 2, the shutters are control to select a light source.

The shutter 304 set in an optical path of the semiconductor laser 303 which oscillates a laser beam having a wavelength of 780 nm is opened to irradiate the sample 1 with a sighting laser beam based on a command from the computer 500. It is to be noted that the shutters 304 corresponding to the other lasers are closed.

In a step 3, the sample is sighted.

Since a laser spot 602 is displayed on the monitor 501, the electric stage 102 is driven to move the cell to a target position in such a manner that a desired position on the cell is irradiated with the laser spot 602. In this embodiment, the nucleus of the cell is sighted. It is to be noted that the nucleus is marked with DRAQ5, and hence no excitation occurs by the semiconductor laser 303 which oscillates a laser beam having a wavelength of 780 nm. Therefore, a color of the sample 1 is not degraded while sighting a target position.

In a step 4, a three-dimensional image is obtained.

The focal plane at the step 1 is changed to acquire XYZ images so that a size of the nucleus is ascertained, and a three-dimensional image shown in FIG. 12 is obtained based on these images. As a result, an image 602 of the laser spot having a wavelength of 780 nm and images of the nucleus 600 marked with DRAQ5 and the microtubule 601 marked with GFP are displayed, and whether the measurement spot 602 is placed at a desired position is conformed. The control advances to the next step if the spot is placed at the desired position, and the steps 1 to 4 are repeated if it is not.

In a step 5, the optical elements which are not required for fluorescence photometry are moved away.

The fluorescence observation cube 108 and the beam splitter 111 are deviated from the optical path.

In a step 6, the shutters are controlled to select a light source.

The shutter 304 set in the optical path of the semiconductor laser 302 which oscillates a laser beam having a wavelength of 780 nm is closed, and the shutter 304 set in the optical path of the semiconductor laser 302 which oscillates a laser beam having a wavelength of 635 nm is opened. Further, the shutter 304 set in the optical path of the semiconductor laser 301 which oscillates a laser beam of 488 nm is also closed.

In a step 7, fluorescence is optically measured.

Fluorescence photometry is started to transfer photometric data to the computer 500.

In a step 8, the shutters are controlled.

Upon completion of photometry, the shutter 304 set in the optical path of the semiconductor laser 302 which oscillates a laser beam having a wavelength of 635 nm is closed.

Although the example of fluorescence photometry of the nucleus marked with DRAQ5 has been explained in this embodiment, the semiconductor laser 301 which oscillates a laser beam having a wavelength of 488 nm may apply the laser beam to optically measure the microtubule marked with GFP, or photometry may be carried out while switching both the measurement targets. It is to be noted that the above operation steps are just an example, and the present invention is not restricted thereto.

An important matter is the structure which can include and realize steps of enabling at least two-dimensionally confirming a measurement region of a spot, starting fluorescence photometry if a target spot region is sighted and repositioning the spot region if it is not sighted.

It is to be noted that the system which carries out the fluorescent correlation spectroscopic photometry has been taken as an example in each of the foregoing embodiment, but the present invention is not of course restricted thereto, and the present invention can be applied to all apparatuses as long as they are apparatuses which must assuredly perform fluorescence photometry with respect to a target measurement region.

[Effects of Fourth Embodiment]

According to the fourth embodiment, in fluorescence photometry using the confocal laser scanning microscope, a sighting position can be matched with a measurement position to improve reliability of data.

Characteristic points of the present invention will now be described.

In each of the foregoing embodiments, as means for switching fluorescence photometry and imaging, an imaging optical path is set to be reflected from a main optical path, and a fluorescence photometry optical path is set to travel along the main optical path. That is, such means is the beam splitter 206 in the first embodiment, the total-reflection mirror 212 in the second embodiment and the beam splitter 111 in the fourth embodiment.

There is a big reason for adoption of such a structure. That is because, when this structure is reversed, the beam splitter is inserted into the optical path to perform fluorescence photometry in case of imaging both a beam spot position and a sample image, but angles of the beam splitter and the mirror cannot be set to be completely equal to each other, and hence a precedent sighting position cannot be completely irradiated at the time of switching to the mirror for fluorescence photometry even if the beam splitter is inserted in the optical path to set the spot sight on a target sample position.

On the other hand, when the imaging optical path is reflected like this embodiment, a sighting position does not deviate at the time of fluorescence photometry even if the reflecting means is moved away from the optical path. A point to notice is to accurately produce parallel glass sheets of the reflecting means 206 and 111 without forming a wedge.

Taking FIG. 1 of PCT National Publication No. 2003-524180 as an example can facilitate understanding.

If fluorescence photometry is carried out based on FU without losing a quantity of fluorescence, the mirror is selected for a diverging optical path. If the beam splitter and the mirror are configured to be switched to/from each other (although such a description is not given in this PCT National Publication No. 2003-524180), reflection angles of the mirror and the beam splitters cannot be completely matched with each other, and hence a sight cannot be accurately taken on a position.

The present invention can be represented as follows based on the foregoing embodiments.

(1) A fluorescence photometric apparatus comprising at least: a light source; light irradiating means for condensing light from the light source on a sample by means of an objective lens and irradiating the sample with the condensed light; and a photodetector which detects fluorescence emitted from the sample, wherein the fluorescence photometric apparatus includes: illuminating means for obtaining a sample image; position adjusting means for adjusting a relative position of the sample and a light spot position condensed by the light irradiating means; and imaging means for simultaneously two-dimensionally or three-dimensionally imaging both the sample image an the light spot image from the light irradiating means condensed on the sample.

The imaging means is represented as the CCD camera 400 in the first to third embodiments and as the confocal laser scanning microscope module 800 in the fourth embodiment.

(2) The fluorescence photometric apparatus characterized in that reflecting means is provided in an optical path extending from the objective lens to the photodetector, and the reflecting means at least partially reflects both light forming the sample image and light from the light source transmitted through or reflected by or scattered by the sample so that both lights travel toward the imaging means.

The reflecting means is represented as the beam splitter 206, the total-reflection mirror 212, the beam splitter 206 and the beam splitter 111 in the first to fourth embodiments.

(3) The fluorescence photometric apparatus characterized in that the reflecting means includes a partially transmitting optical element or a beam splitter such as a dichroic mirror having wavelength characteristics.

(4) The fluorescence photometric apparatus characterized in that the beam splitter is fixedly arranged to at least partially transmit fluorescence from the sample therethrough to be led to the photodetector.

The beam splitter 206 in the third embodiment is fixedly arranged.

(5) The fluorescence photometric apparatus characterized in that the reflecting means includes a total-reflection mirror configured to be inserted into/removed from an optical path, and light from the light source is led to an optical path between the objective lens and the total-reflection mirror.

The total-reflection mirror 212 is provided in the second embodiment.

(6) The fluorescence photometric apparatus characterized in that the reflecting means can be inserted into/removed from an optical path by switching means and is arranged to lead fluorescence from the sample to the photodetector when the reflecting means deviates from the optical path.

The beam splitter 206, the total-reflection mirror 212 and the beam splitter 111 in the first, third and fourth embodiments can be inserted into/removed from an optical path by switching means.

(7) The fluorescence photometric apparatus according to claim 2, wherein a pin hole is arranged at a position which is optically conjugated with a light spot condensed by the light irradiating means between the reflecting means and the photodetector.

The pin hole 207 is provided in the first, second and fourth embodiments.

(8) The fluorescence photometric apparatus characterized in that the pin hole is arranged coaxially with an optical path in which the reflecting means is arranged.

(9) The fluorescence photometric apparatus characterized in that at least the reflecting means and the pin hole are constituted as an optical module on a common frame.

The optical module in the first, second and fourth embodiments includes the reflecting means and the pin hole. Here, the optical module means a unit which includes a plurality of optical elements and is integrally constituted.

(10) The fluorescence photometric apparatus characterized in that a connecting portion to which the imaging means can be connected is provided in the optical module.

(11) The fluorescence photometric apparatus characterized in that the optical module includes the imaging means.

(12) The fluorescence photometric apparatus characterized in that the illuminating means includes a reflection type illumination device and light from the illuminating means is led to an optical path between the reflecting means and the objective lens.

The reflecting fluorescence illumination optical system 104 in the first and second embodiments is a reflection type illumination device.

(13) The fluorescence photometric apparatus characterized in that the illuminating means includes a transmission type illumination device.

The transmitting illumination optical system 105 in the first to third embodiments is a transmission type illumination device.

(14) The fluorescence photometric apparatus characterized in that the imaging means is a confocal laser scanning microscope module.

(15) The fluorescence photometric apparatus characterized in that the confocal laser scanning microscope module includes three-dimensional image configuring means for configuring both a sample image and an image of a light spot from the light irradiating means condensed on the sample, into a three-dimensional image based on a plurality of two-dimensional images.

(16) The fluorescence photometric apparatus characterized in that the light irradiating means comprises light source selecting means which includes a light source for photometry which is used for photometry of fluorescence having different wavelengths and a light source for photometric position confirmation and selectively applies light from these light sources toward the sample.

The shutters 304 in the first, second and fourth embodiments selectively apply lights from the light sources toward the sample.

(17) The fluorescence photometric apparatus characterized in that the light source for photometric position confirmation is a laser or an LED.

(18) The fluorescence photometric apparatus characterized in that the light source for photometric position confirmation emits light having a wavelength longer than that of light from the light source for photometry.

(19) The fluorescence photometric apparatus characterized in that the light source selecting means operates in cooperation with the switching means and includes controlling means for making control in such a manner that the reflecting means is inserted into the optical path when the light source for photometric position confirmation is selected and the reflecting means is moved away from the optical path when the light source for photometry is selected.

(20) The fluorescence photometric apparatus characterized in that the light irradiating means includes introducing means for introducing light from the light source for photometry and light from the light source for photometric position confirmation, to a single-mode fiber.

It is to be noted that the present invention is not restricted to the foregoing embodiments, and it can be embodied by modifying constituent elements without departing from the scope thereof on an embodying stage. Furthermore, various kinds of inventions can be formed by appropriately combining a plurality of constituent elements disclosed in the foregoing embodiments. For example, some constituent elements can be eliminated from all constituent elements described in the foregoing embodiments. Moreover, constituent elements in the different embodiments can be appropriately combined.

What is claimed is:

1. A fluorescence photometric apparatus comprising at least:
   a light source;

a light irradiating unit configured to condense light from the light source on a sample by means of an objective lens and irradiating the sample with the condensed light; and a photodetector which detects fluorescence emitted from the sample, wherein the fluorescence photometric apparatus includes:

an illuminating unit configured to obtaining a sample image;

a position adjusting unit configured to adjusting a relative position of the sample and a position of a light spot condensed by the light irradiating unit; and an imaging unit configured to simultaneously two-dimensionally or three-dimensionally imaging both the sample image and an image of the light spot from the light irradiating unit configured to condensing the light on the sample, wherein a reflecting unit is provided in an optical path extending from the objective lens to the photodetector, and the reflecting unit at least partially reflects both light forming the sample image and light from the light source transmitted through, reflected by or scattered by the sample so that the lights travel toward the imaging unit, and wherein the reflecting unit includes a partially transmitting optical element or a beam splitter having wavelength characteristics.

2. The fluorescence photometric apparatus according to claim 1, wherein the beam splitter is fixedly arranged to at least partially transmit fluorescence from the sample therethrough and lead it to the photodetector.

3. A fluorescence photometric apparatus comprising at least:

a light source;

a light irradiating unit configured to condense light from the light source on a sample by means of an objective lens and irradiating the sample with the condensed light; and a photodetector which detects fluorescence emitted from the sample, wherein the fluorescence photometric apparatus includes:

an illuminating unit configured to obtaining a sample image;

a position adjusting unit configured to adjusting a relative position of the sample and a position of a light spot condensed by the light irradiating unit; and an imaging unit configured to simultaneously two-dimensionally or three-dimensionally imaging both the sample image and an image of the light spot from the light irradiating unit configured to condensing the light on the sample, wherein a reflecting unit is provided in an optical path extending from the objective lens to the photodetector, and the reflecting unit at least partially reflects both light forming the sample image and light from the light source transmitted through, reflected by or scattered by the sample so that the lights travel toward the imaging unit, and wherein the reflecting unit includes a total-reflection mirror configured to be inserted into/removed from an optical path, and light from the light source is led to an optical path between the objective lens and the total-reflection mirror.

4. A fluorescence photometric apparatus comprising at least:

a light source;

a light irradiating unit configured to condense light from the light source on a sample by means of an objective lens and irradiating the sample with the condensed light; and a photodetector which detects fluorescence emitted from the sample, wherein the fluorescence photometric apparatus includes:

an illuminating unit configured to obtaining a sample image;

a position adjusting unit configured to adjusting a relative position of the sample and a position of a light spot condensed by the light irradiating unit; and an imaging unit configured to simultaneously two-dimensionally or three-dimensionally imaging both the sample image and an image of the light spot from the light irradiating unit configured to condensing the light on the sample, wherein a reflecting unit is provided in an optical path extending from the objective lens to the photodetector, and the reflecting unit at least partially reflects both light forming the sample image and light from the light source transmitted through, reflected by or scattered by the sample so that the lights travel toward the imaging unit, and wherein the reflecting unit is configured to be inserted into/removed from an optical path by a switching unit and arranged to lead fluorescence from the sample to the photodetector when the reflecting unit deviates from the optical path.

5. A fluorescence photometric apparatus comprising at least:

a light source;

a light irradiating unit configured to condense light from the light source on a sample by means of an objective lens and irradiating the sample with the condensed light; and a photodetector which detects fluorescence emitted from the sample, wherein the fluorescence photometric apparatus includes:

an illuminating unit configured to obtaining a sample image;

a position adjusting unit configured to adjusting a relative position of the sample and a position of a light spot condensed by the light irradiating unit; and an imaging unit configured to simultaneously two-dimensionally or three-dimensionally imaging both the sample image and an image of the light spot from the light irradiating unit configured to condensing the light on the sample, wherein a reflecting unit is provided in an optical path extending from the objective lens to the photodetector, and the reflecting unit at least partially reflects both light forming the sample image and light from the light source transmitted through, reflected by or scattered by the sample so that the lights travel toward the imaging unit, and wherein a pin hole is arranged at a position optically conjugated with a light spot condensed by the light irradiating unit between the reflecting unit and the photodetector.

6. The fluorescence photometric apparatus according to claim 5, wherein the pin hole is arranged coaxially with an optical path in which the reflecting unit is arranged.

7. The fluorescence photometric apparatus according to claim 5, wherein at least the reflecting unit and the pin hole are constituted as an optical module on a common frame.

8. The fluorescence photometric apparatus according to claim 7, wherein a connecting portion configured to be connected with the imaging unit is provided in the optical module.

9. The fluorescence photometric apparatus according to claim 7, wherein the optical module includes the imaging unit.

10. A fluorescence photometric apparatus comprising at least:
a light source:
a light irradiating unit configured to condense light from the light source on a sample by means of an objective lens and irradiating the sample with the condensed light; and
a photodetector which detects fluorescence emitted from the sample,
wherein the fluorescence photometric apparatus includes:
an illuminating unit configured to obtaining a sample image;
a position adjusting unit configured to adjusting a relative position of the sample and a position of a light spot condensed by the light irradiating unit; and
an imaging unit configured to simultaneously two-dimensionally or thee-dimensionally imaging both the sample image and an image of the light spot from the light irradiating unit configured to condensing the light on the sample,
wherein the imagine unit is a confocal laser scanning microscope module, and wherein the confocal laser scanning microscope module includes thee-dimensional image configuring unit configured to configure both the sample image and the image of the light spot from the light irradiating unit condensed on the sample, into a thee-dimensional image based on a plurality of two-dimensional images.

11. A fluorescence photometric apparatus comprising at least:
a light source;
a light irradiating unit configured to condense light from the light source on a sample by means of an objective lens and irradiating the sample with the condensed light; and
a photodetector which detects fluorescence emitted from the sample,
wherein the fluorescence photometric apparatus includes:
an illuminating unit configured to obtaining a sample image;
a position adjusting unit configured to adjusting a relative position of the sample and a position of a light spot condensed by the light irradiating unit; and
an imaging unit configured to simultaneously two-dimensionally or three-dimensionally imaging both the sample image and an image of the light spot from the light irradiating unit configured to condensing the light on the sample,
wherein the light irradiating unit comprises light source selecting unit which includes a light source for photometry which is used for photometry of fluorescence having different wavelengths and a light source for photometric position confirmation, and selectively applies lights from the light sources toward the sample.

12. The fluorescence photometric apparatus according to claim 11, wherein the light source for photometric position confirmation is a laser or an LED.

13. The fluorescence photometric apparatus according to claim 11, wherein the light source for photometric position confirmation emits light having a wavelength longer than that of light from the light source for photometry.

14. The fluorescence photometric apparatus according to claim 11, wherein the light source selecting unit operates in cooperation with the switching unit and includes a controlling unit configured to make control in such a manner that the reflecting unit is inserted into an optical path when the light source for photometric position confirmation is selected and the reflecting unit is moved away from the optical path when the light source for photometry is selected.

15. The fluorescence photometric apparatus according to claim 11, wherein the light irradiating unit includes an introducing unit configured to introduce light from the light source for photometry and light from the light source for photometric position confirmation, to a single-mode fiber.

* * * * *